United States Patent [19]  
Engel

[11] 4,341,796  
[45] * Jul. 27, 1982

[54] CONTROL OF ACARIDS WITH BIPHENYLMETHYL PERHALOALKYLVINYLCYCLO-PROPANECARBOXYLATES

[75] Inventor: John F. Engel, Medina, N.Y.

[73] Assignee: FMC Corporation, Philadelphia, Pa.

[*] Notice: The portion of the term of this patent subsequent to Dec. 9, 1997, has been disclaimed.

[21] Appl. No.: 195,035

[22] Filed: Oct. 8, 1980

Related U.S. Application Data

[63] Continuation-in-part of Ser. No. 52,043, Jun. 25, 1979, Pat. No. 4,238,505, and a continuation-in-part of Ser. No. 927,198, Jul. 24, 1978, abandoned, and Ser. No. 870,973, Jan. 20, 1978, abandoned.

[51] Int. Cl.³ ............... A01N 37/00; A01N 37/08
[52] U.S. Cl. ............................................. 424/305
[58] Field of Search ............... 560/124; 424/305, 306

[56] References Cited

U.S. PATENT DOCUMENTS 4,130,657 12/1978 Plummer ........................ 424/305
4,157,447  6/1979 Engel ............................. 560/8
4,214,004  7/1980 Plummer ........................ 424/305

FOREIGN PATENT DOCUMENTS 858137  2/1978 Belgium .
858163  2/1978 Belgium .
863151  7/1978 Belgium .
52-14749 2/1977 Japan .

Primary Examiner—Douglas W. Robinson  
Attorney, Agent, or Firm—Robert L. Andersen; H. Robinson Ertelt

[57] ABSTRACT

Acaricidal use is disclosed and exemplified for compounds of the general formula

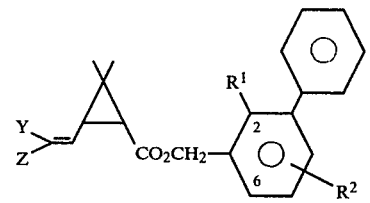

in which one of Y and Z is a trifluoromethyl group, the other is a halogen atom, $R^1$ is lower alkyl or halogen, $R^2$ is hydrogen, halogen, or lower alkyl, or $R^1$ and $R^2$ are both hydrogen.

5 Claims, No Drawings

CONTROL OF ACARIDS WITH BIPHENYLMETHYL PERHALOALKYLVINYLCYCLOPROPANECARBOXYLATES

This application is a continuation-in-part of copending U.S. Ser. No. 052,043, filed June 25, 1979, now U.S. Pat. No. 4,238,505, a continuation-in-part of Ser. Nos. 927,198, filed July 24, 1978, and 870,973, filed Jan. 20, 1978, both now abandoned.

The present invention is directed to the use of biphenylmethyl perhaloalkylvinylcyclopropanecarboxylates for controlling acarids such as mites and ticks.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. A noteworthy advance in this area was the discovery by Elliott et al. of certain highly active dihalovinylcyclopropanecarboxylates such as permethrin, the common name for 3-phenoxybenzyl 3-(2,2-dichloroethenyl)-2,2-dimethylcyclopropanecarboxylate. This class of compounds, set forth in U.S. Pat. No. 4,024,163, issued May 17, 1977, exhibits substantially improved photostability when compared with previously available cyclopropanecarboxylates, and high levels of foliar insecticidal activity, but has not demonstrated significant levels of activity against acarids.

U.S. Pat. Nos. 4,130,657 and 4,214,004 to Plummer disclose that that certain unsubstituted and substituted biphenylmethyl esters of 3-(2,2-dihaloethenyl)-2,2-dimethylcyclopropanecarboxylic acid are active against insects and acarids.

Prior copending application U.S. Ser. No. 052,043 describes and claims the general insecticidal utility for biphenylmethyl perhaloalkylvinylcyclopropanecarboxylates and reports a high level of foliar aphid activity. While that application discloses a broad utility in controlling household, veterinary, and crop insects, it has now been found that, when applied to surfaces to which acarids are attracted and upon which they feed, certain biphenylmethyl perhaloalkylvinylcyclopropanecarboxylates are extremely active in killing and/or repelling acarids. The present invention thus provides a method for control of acarids in veterinary and crop applications utilizing the biphenylmethyl perhaloalkylvinylcyclopropanecarboxylates set forth below.

In this application, the term "lower", as applied to a hydrocarbyl group means having 1-6 carbon atoms, straight or branched chain, preferably 1-4 carbon atoms. The term "halo" or "halogen" means bromine, chlorine, or fluorine. These definitions are applicable throughout the specification and claims except where a contrary meaning is clearly indicated.

The method of this invention utilizes cyclopropanecarboxylates of the general formula

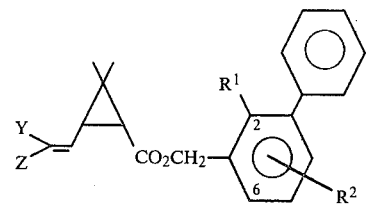

wherein one of Y and Z is a trifluoromethyl group, the other of Y and Z is a halogen atom, preferably chlorine; $R^1$ is lower alkyl or halogen, $R^2$ is hydrogen, halogen or lower alkyl, preferably at position 6 when other than hydrogen, or $R^1$ and $R^2$ are both hydrogen. Compounds of particular interest are those shown below:

| Compound | Z | Y | $R^1$ | $R^2$ | Isomer |
|---|---|---|---|---|---|
| A | $CF_3$ | Cl | $CH_3$ | H | cis |
| B | $CF_3$ | Cl | F | F | cis |
| C | $CF_3$ | Cl | $CH_3$ | $CH_3$ | cis |
| D | $CF_3$ | Cl | Cl | Cl | cis, trans (E, Z) |
| E | $CF_3$ | Cl | Cl | H | cis |
| F | $CF_3$ | Cl | Br | H | cis |
| G | $CF_3$ | Cl | $C_2H_5$ | H | cis |
| H | $CF_3$ | Cl | H | H | cis |

The foregoing compounds and certain intermediates therefor exist as cis and trans geometrical isomers, i.e., the carboxy and the substituted vinyl groups at the 1 and 3 positions of the cyclopropane ring are either cis or trans with respect to each other. Preparation of such compounds will usually yield a mixture of cis and trans isomers, designated cis,trans, in which the ratio of cis to trans may vary over a wide range. For purposes of this application the designations cis and trans are assigned in accordance with P. E. Burt, et al., *Pestic. Sci.*, 5 791–799 (1974). The compounds of this invention may also exist as E or Z isomers or as mixtures of E and Z isomers, designated E,Z, depending on the spatial relationship of substituents on the α-carbon of the vinyl group to those on the β-carbon of the vinyl group. The compounds also exist as enantiomers and diasteriomers as is well known to those skilled in the art.

In the cyclopropanecarboxylate art it is known there may be substantial differences in the level of insecticidal activity between the various forms in which the compounds may exist. For example, as between the cis and trans isomers of a given cyclopropanecarboxylate, the cis isomer is usually more active than the trans and also more active than the cis,trans mixture. Similar differences in activity may also occur with respect to the E and Z isomers, and between the various enantiomers and diasteriomers.

Unless a contrary intent is expressed, the invention embodies and includes all compounds in which the carboxy and substituted vinyl groups at the 1 and 3 positions of the cyclopropane ring are cis or trans, or a mixture of cis and trans configuration with respect to each other. Similarly, the individual E and Z isomers, as well as the mixtures, are also contemplated by and within the scope of the present invention. The various spatial arrangements of these isomers are also included individually and collectively within the scope of the invention.

The compounds may be prepared from alkanoates of the formula

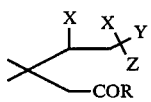

in which Y and Z are defined as above; R is lower alkoxy; such as methoxy or ethoxy; and X is chloro or bromo. Example 1 illustrates a method for preparation of the alkanoate intermediates of formula II whereby a lower alkyl 3,3-dimethyl-4-pentenoate is allowed to react with a compound of the formula X₂C(Y)(Z) wherein X, Y, and Z are as defined above.

Dehydrohalogenation of the compound of formula II followed, if necessary, by hydrolysis of the ester and, also if necessary, halogenation of the resulting carboxyl group gives a compound of the formula

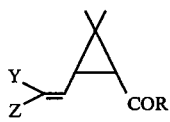

in which R is lower alkoxy, hydroxy, halogen and Y and Z are as defined above. The dehydrohalogenation reaction may proceed through one or more intermediates of the formulas

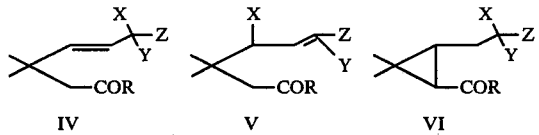

and may be conducted in a single step by removal of 2 equivalents of hydrogen halide, HX, to give a compound of formula III directly or in multiple steps under conditions allowing a sequential removal of the two equivalents of HX in separate reactions. These intermediates or mixtures thereof may be recovered if desired. The compound of formula III is then converted to the compound of formula I by methods known to the art, for example, by esterifying or transesterifying with HOR¹ or, when R is hydroxy, by reaction with R¹X¹ in which X¹ is a suitable leaving group such as bromine.

The examples which follow illustrate preparation of these compounds in accordance with the general methods described above. In the examples all temperatures are in degrees centigrade, all pressures are in mm. Hg, and reduced pressure for concentrations of liquid was produced by a water aspirator unless otherwise specified.

The intermediates and final products are fully described and prepared in accordance with the teaching of prior copending U.S. application Ser. No. 052,043, incorporated herein by reference.

The following example is illustrative of the preparation of the compounds for use in the presently claimed method.

EXAMPLE 1

SYNTHESIS OF [1,1'-BIPHENYL]-3-YLMETHYL CIS-3-(2-CHLORO-3,3,3-TRIFLUORO-1-PROPENYL)-2,2-DIMETHYLCYCLO-PROPANECARBOXYLATE

To a solution of 32.5 g (0.58 mole) of potassium hydroxide in 200 ml of water was added 112 g (0.46 mole) of cis-3-(2-chloro-3,3,3-trifluoro-1-propenyl)-2,2-dimethylcyclopropanecarboxylic acid. To the resulting solution was added 1000 ml of heptane. This mixture was heated at reflux until 200 ml of water was collected in a Dean-Stark trap.

The reaction mixture was cooled to 50° C. and 113.6 g (0.46 mole) of 3-bromomethyl[1,1'-biphenyl] and 1000 ml of acetonitrile were added. 3-Bromomethyl[1,1'-biphenyl] may be prepared according to the method disclosed in U.S. Pat. No. 4,130,657. The resulting mixture was refluxed for 16 hours at which time 4.5 g (0.04 mole) of 1,4-diazabicyclo[2,2,2]octane was added. Refluxing was continued for an additional 4 hours, then the reaction mixture was cooled to room temperature and 600 ml of water was added. The aqueous layer was separated and was washed once with heptane. The heptane wash and the organic layer were combined, washed once with water, dried over anhydrous sodium sulfate, filtered, and the filtrate concentrated under reduced pressure to give 198 g of residual oil.

The residual oil was passed through a 1200 g column of silica gel using successively 4000 ml of hexane, 2000 ml of hexane/diethyl ether (1/1), 1000 ml of hexane/diethyl ether (½) and finally diethyl ether to elute the product. The appropriate fractions were combined and stripped of solvent to give 113.2 g of semi-pure product which was passed through a second 1200 g silica gel column. The product was eluted successively with 3500 ml of hexane, 2400 ml of hexane/diethyl ether (7/1), and 1800 ml of hexane/diethyl ether (5/1), the appropriate fractions were combined to yield 82.9 g of [1,1'-biphenyl]-3-ylmethyl cis-3-(2-chloro-3,3,3,-trifluoro-1-propenyl)-2,2-dimethylcyclopropanecarboxylate as an orange oil. Analysis by liquid chromatography indicated a purity of 93% and a cis/trans isomer ratio of 98/2. The nmr and ir spectra were consistent with the proposed structure, and were identical to a previously prepared sample, the boiling point of which was 117°–123° C./0.05 mm.

Analysis calc'd for $C_{22}H_{20}ClF_3O_2$: C 64.63, H 4.92; Found: C 64.70, H 4.97.

In accordance with the method of this invention, an acaricidal amount of the compound I, as defined above, is applied to the locus to which acarids are attracted or upon which they feed, i.e., to the surface of plants or seeds or topically for veterinary application.

The compounds are useful for the control of acarids such as ticks or mites on domestic animals, household pets or agricultural crops, and may be applied as technical material or as a formulated product. Typical agricultural formulations include compositions of the active ingredient in combination with an agriculturally acceptable carrier or extender, preferably with a surface-active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of the active ingredient depending upon the particular agent used, the additives and carriers used, other active ingredients and the desired mode of application. With due consideration of these factors, the active ingredient of a typical formulation may, for example, be suitably present at a concentration of about 0.1% up to about 99.5% by weight of the formulation. An agriculturally acceptable carrier may comprise about 99.5% by weight to as low as about 0.5% by weight of the formulation. Compatible surface-active agents, if employed in the formulation, may be present at various concentrations, suitably in the range of 1% to 30% by weight of the formulation.

The formulation may be used as such or diluted to a desired use dilution with a diluent or carrier suitable for facilitating dispersion of the active ingredients. The concentration of the active ingredient in the use dilution may be in the range of about 0.01 to about 10% by weight.

Many variations of spraying, dusting, and controlled or slow release compositions of a type known in the art may be used by substituting or adding a compound of this invention into the compositions known or apparent to the art.

The compounds of this invention may be formulated and applied with other compatible active agents.

In applying these compounds, whether alone or with other agricultural chemicals, an effective acaricidal amount of the active ingredient may be applied to kill mites and ticks feeding on the treated surface or come into physical contact with the active ingredient. The compounds are also highly repellent to acarids, particularly mites. Accordingly, an amount sufficient to repel may also be applied to a surface to which acarids are attracted even though this amount may be lower than the amount or concentration required to kill. The use of a repellent amount is particularly useful in repelling ticks and mites from pets and other domestic animals when topically applied. The application rate will thus vary widely depending on the choice of compound, the formulation, mode of application and the results desired.

The compounds of this invention were tested for activity against twospotted spider mite (*Tetranychus urticae* [Koch]) by foliar application of the test compound. The test compound was dissolved in a small amount of acetone, and the acetone solution was dispersed in water containing 0.25 percent octylphenoxypolyethoxyethanol to make solutions having various concentrations of active ingredient. The activity against twospotted spider mite was evaluated on pinto bean plants whose leaves were sprayed with test solution after infestation with adult mites. Following application the tests were maintained in a holding room at 20° C. and 50% relative humidity for an exposure period of at least 48 hours. At the end of this time the dead and living mites were counted, and the percent kill was calculated. It was noted that the mites not killed had left the treated surfaces, indicating the repellency of the test compounds.

The percent kill at various concentrations is reported in Table I in which the letter designations correspond to structures set forth above. The compounds of this invention were highly active against mites.

TABLE I

| Rate (ppm) | A | B | C | D | E | F | G | H |
|---|---|---|---|---|---|---|---|---|
| 1000 | | | | | | | | |
| 750 | | | | | | | | |
| 500 | 100 | | 100 | 100 | 100 | 100 | | |
| 312 | | | | | | | | 100 |
| 250 | | | | | | | | |
| 156 | | | | | | | | 98 |
| 78 | | | | | | | | 100 |
| 64 | | 64 | 100 | | 100 | $100^b$ | 81 | |
| 39 | | | | | | | | 50 |
| 32 | | | 93 | | 51 | 47 | 25 | |
| 16 | $99^b$ | | 92 | | $49^b$ | $30^b$ | $32^b$ | |
| 8 | $90^b$ | | 86 | | $9^b$ | | | |
| 4 | $70^b$ | | 43 | | | | | |
| 2 | $42^b$ | | | | | | | |
| 1 | $33^b$ | | | | | | | |

$^b$Average of more than one test

I claim:

1. A method of controlling acarids which comprises applying to said acarids or a locus where control is desired an acaricidal or acarid repellent amount of a compound of the formula

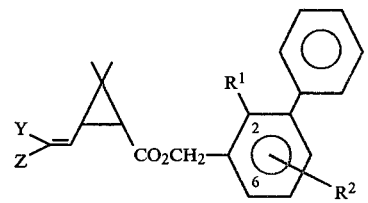

wherein one of Y and Z is trifluoromethyl, and the other of Y and Z is halogen, $R^1$ is halogen or lower alkyl and $R^2$ is hydrogen, halogen or lower alkyl, or $R^1$ and $R^2$ are both hydrogen.

2. The method of claim 1 in which $R^2$ is hydrogen, 6-methyl, or 6-halo.

3. The method of claim 1 in which $R^1$ is methyl and $R^2$ is hydrogen or 6-methyl.

4. The method of claim 3 in which $R^2$ is hydrogen.

5. The method of claim 1, 2, 3 or 4 in which an acaricidal amount of the compound of said claim is applied to the above ground portions of agricultural crops.

* * * * *